(12) United States Patent
Pavcnik et al.

(10) Patent No.: US 6,325,819 B1
(45) Date of Patent: *Dec. 4, 2001

(54) ENDOVASCULAR PROSTHETIC DEVICE, AN ENDOVASCULAR GRAFT PROTHESIS WITH SUCH A DEVICE, AND A METHOD FOR REPAIRING AN ABDOMINAL AORTIC ANEURYSM

(75) Inventors: Dusan Pavcnik; Frederick S. Keller; Barry T. Uchida, all of Portland, OR (US)

(73) Assignee: Cook Incorporated, Bloomington, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/697,057

(22) Filed: Aug. 19, 1996

(51) Int. Cl.$^7$ .............................. A61F 11/00; A61F 2/06
(52) U.S. Cl. ................. 623/1.11; 623/1.35; 606/108; 606/198
(58) Field of Search ................. 623/1, 12, 1.15, 623/1.16, 1.2, 1.35, 1.36, 23.7, 1.13, 1.14, 1.11; 606/108, 198, 191, 192, 194, 195

(56) References Cited

U.S. PATENT DOCUMENTS

| | | |
|---|---|---|
| 4,662,885 | 5/1987 | DiPisa, Jr. . |
| 5,316,023 | 5/1994 | Palmaz et al. . |
| 5,375,612 | * 12/1994 | Cottenceau et al. ............... 128/899 |
| 5,562,724 | * 10/1996 | Vorwerk et al. ....................... 623/1 |

FOREIGN PATENT DOCUMENTS

| | | |
|---|---|---|
| 19509464 | 6/1996 | (DE) . |
| 0423916 | 4/1991 | (EP) . |
| 0539237 | 4/1993 | (EP) . |
| 0565395 | 10/1993 | (EP) . |
| 9516406 | 6/1995 | (WO) . |
| 9521592 | 8/1995 | (WO) . |
| 9625897 | 8/1996 | (WO) . |

* cited by examiner

*Primary Examiner*—Paul Prebilic
(74) *Attorney, Agent, or Firm*—Richard J. Godlewski

(57) ABSTRACT

An endovascular graft prosthesis for arrangement at an aneurysm positioned in the vicinity of a bifurcation in an arterial system having a main lumen and a first and a second branch lumen. The endovascular graft prosthesis includes a prosthetic device with at least one expandable tubular frame body for arrangement in the main lumen and a first and a second graft limb. The frame body is contractible into a first shape with a smaller diameter for introduction to a vascular site upstream of the aneurysm and is radially expandable into a second shape having a larger diameter and an inner lumen. The frame body is provided with a covering which extends across the inner lumen of the tubular frame body and has two apertures each of which has a diameter of less than half the larger diameter of the frame body. The first and second limbs have a cranial end for mounting at one of the apertures and a caudal end for arrangement in one of the branch lumens. The covering is a hindrance to blood flowing past the frame body except for blood flowing into the first and second graft limbs mounted at the two apertures.

25 Claims, 5 Drawing Sheets

ENDOVASCULAR PROSTHETIC DEVICE, AN ENDOVASCULAR GRAFT PROTHESIS WITH SUCH A DEVICE, AND A METHOD FOR REPAIRING AN ABDOMINAL AORTIC ANEURYSM

TECHNICAL FIELD

This invention relates generally to medical devices and, more particularly, to an endovascular prosthetic device including at least one expandable tubular frame body provided with at least one covering of bio-compatible material. The frame body is contractible into a first shape with a small diameter for introduction to a vascular site and is radially expandable into a second shape having a larger diameter and an inner lumen.

The present invention also relates to an endovascular graft prosthesis for arrangement at an aneurysm positioned in the vicinity of a bifurcation in an arterial system having a main lumen and a first and a second branch lumen. The graft prosthesis includes an endovascular prosthetic device with at least one expandable tubular frame body for arrangement in the main lumen and a first and a second graft limb. The frame body is contractible for introduction to a vascular site upstream of the aneurysm.

BACKGROUND OF THE INVENTION

An aortic aneurysm effects nearly 200,000 Americans annually and presents a significant risk of mortality to a patient. Death often occurs when the aneurysm ruptures. Open, invasive, elective surgery to repair an aortic aneurysm also presents a significant risk of mortality and has been reported to be in the two to three percent. As a result, minimally invasive surgical repair of aortic aneurysms are highly desirable and are preferred. An endovascular graft prosthesis of this kind and provided with a prosthetic device of the above kind is known from EP 0539237. This graft prosthesis has a main body connected to two graft limbs. During introduction all three elements of the prosthesis have to be placed inside a catheter with the consequence that the catheter must have a large diameter, which makes true percutaneous insertion into the femoral arteries impossible. It is also a disadvantage that the frame body of the prosthetic device is covered by the cranial end of the graft main body on its periphery, because the graft main body restricts the maximum radial expansion of the frame body and thus limits the radial pressure of the frame body on the aorta.

W095/16406 discloses another endovascular graft prosthesis for abdominal aorta aneurysm repair comprising a bag-shaped graft main body and two graft limbs which are separately femorally introduced and inserted through outlet openings in the bottom of the bag-shaped main body and mounted inside the bag. The frame body of the prosthetic device is also in this case on its periphery covered by the cranial end of the graft main body, and in the radially compressed shape of the frame body the surrounding graft material is positioned outside the frame body adding to the diameter of the compressed device, and thus requiring a larger sized introducer catheter. Furthermore, when the limbs are to be positioned it may be difficult to catch the outlet openings in the loosely downhanging lower portion of the bag.

U.S. Pat. No. 5,316,023 suggests a method for repairing an abdominal aorta aneurysm by femorally advancing one tube through each iliac artery and positioning the cranial ends of the tubes in the aorta upstream of the aneurysm, whereupon inflatable balloons are used to expand said cranial ends into contact with each other and the aorta. The expanded tube ends are at risk of creating an incomplete blockage of the blood flow to the aneurysm, in particular in two wedge-shaped areas positioned at opposite sides of the central area of contact between the two tubes.

An abdominal aorta aneurysm requiring repair is a serious and often deadly condition found in patients who are often already weakened by other conditions. The existing minimally invasive techniques for aorta aneurysm repair are only capable of treating from 20 to 30 percent of the total discovered conditions requiring repair, and the failure rate is too high when repair is sought with aid from existing techniques. One particular problem with prior art endovascular graft prosthesis is the risks of leaks of blood past the cranial graft end into the aneurysm. Such leaks may be caused by incomplete occlusion of the aorta lumen when the graft prosthesis is initially mounted in the aorta or may be caused by lacking ability of the graft prosthesis to continuously block for blood leaks past the full periphery of the cranial graft end during a time span of hours or days following the mounting of the graft prosthesis.

SUMMARY OF THE INVENTION

It is an advantage of the invention to provide an endovascular prosthetic device having a frame body with a high ability to remain in contact with a vascular wall, even if the wall changes shape in a local area when the patient moves.

It is a further advantage of the invention to provide a prosthetic device capable of effecting a well defined partial occlusion of a body vessel.

It is yet another advantage of the invention to provide a prosthetic device which can be contracted into a shape with such small outer dimensions that the device can be loaded into a sheath or a catheter having an inner lumen of 14 French or less.

The invention also aims at providing an endovascular graft prosthesis allowing transluminally repair of aneurysms in bifurcated lumens.

It is a further advantage of the invention to device an endovascular graft prosthesis providing low risks of blood leakage.

It is yet another object of the invention to design an endovascular graft prosthesis which is comparatively easy to introduce and mount in the vascular system.

Further objects of the invention appears from the detailed description of preferred embodiments.

In order to achieve these advantages and also further advantages, the prosthetic device is made so that the bio-compatible material covering extends freely and orthogonally across the cross-sectional diameter of the inner lumen of the tubular frame body at both ends thereof and has multiple apertures. Each of the apertures has a diameter of less than half the larger diameter of the frame body, and that the covering is spread out to a substantially plane shape by the expansion of the tubular frame.

By the installation of the frame body at the desired vascular site the covering extending across the cross-sectional diameter of the inner lumen of the frame body at each end is brought to extend across the cross-sectional diameter and thereby occlude the inner lumen of the vessel in the area surrounding the apertures. The amount of covering required to occlude the lumen in a direction transverse to the longitudinal direction of the vessel is substantially smaller than the amount of covering needed to cover the periphery of the frame body. The small amount of covering used in the present device facilitates loading of the device into a small diameter catheter. Another substantial advantage is that the covering only restricts radial expansion of the frame body at the circumferential line described by the outer rim of the covering, whereas the radial expansion of the remaining portion or portions of the frame body is unrestricted by the covering. In these unrestricted portions, the frame body is free to follow shape changes in the vascular wall. The mounting of the covering inside the frame body provides the additional advantage that the covering is prevented from getting locked between the exterior of the frame body and the vascular wall during expansion of the frame body to the second shape. In the prior art devices where the covering is provided on the exterior of the frame body, a folded portion of the covering may become stuck between the frame body and the vascular wall so that full expansion of the frame body is prevented. This risk is not relevant to the present device.

The covering may be mounted at any position on the frame body, e. g., at the middle of the frame body length. This may be an advantage if the vessel occlusion is to be effected at a vascular site where the vessel has a pronounced hourglass-shape. However, the covering is preferably mounted at one or both ends of the tubular body. In some instances it is desirable to use the device with only one occluding covering positioned at the downstream end of the frame body. If an abdominal aneurysm terminates very close to the renal artery branches, the length of the infrarenal aortic portion upstream of the aneurysm is short. The latter device may in this case be positioned with its end carrying the covering on the downstream side of the renal artery branches and its opposite end on the upstream side thereof. As the occlusion of the aorta takes place at the covering, blood flow to the renal artery branches may substantially and uninterruptedly continue down through the open upstream end and out through the open side of the tubular body. Another advantage of the latter device is its ability to be loaded into a small diameter catheter because the covering can be placed in extension of the frame body inside the catheter.

In about 80 percent of abdominal aortic aneurysms requiring repair, the length of the nondilated infrarenal aortic portion upstream of the aneurysm is at least about 2.7 cm. Here it is possible to position the whole prosthetic device downstream of the renal artery branches and at the same time obtain secure positional locking of the frame body to the vascular wall. In this case, the tubular body preferably has at either of its ends one covering each with two apertures. With such a drum-like configuration of the prosthetic device, blood leakage is prevented at two longitudinally separated positions in the artery, so that any leaks past the upstream covering will be stopped by the downstream covering.

It is possible to use a variety of different tubular bodies in the device. Such tubular bodies are conventionally called stents. One example is a tubular body made of several elastic filaments or wires helically wound in opposite directions. The tubular body may be balloon-expandable, but is preferably self-expanding upon release from the introducer catheter. In a preferred embodiment of the device the tubular body comprises a flexible filament formed into a closed zig-zag configuration having an endless series of straight sections joined by bends at opposite ends of said straight sections.

The endovascular graft prosthesis incorporating the prosthetic device is designed so that the frame body is provided with a covering extending across the inner lumen of the tubular frame body and having two apertures, and each of the apertures has a diameter of less than half the larger diameter of the frame body. Furthermore, the first limb has a cranial end for mounting at one of the apertures and a caudal end for arrangement in the first branch lumen, and the second limb has a cranial end for mounting at the other of the apertures and a caudal end for arrangement in the second branch lumen. The covering is a hindrance to blood flowing past the frame body except for blood flowing into the first and second graft limbs mounted at the two apertures.

The three parts of the graft prosthesis, namely the prosthetic device and the first and second limbs, can easily be loaded into small diameter catheters and be introduced femorally into the vascular system. When the prosthetic device has been correctly placed at the desired site and expanded to the second shape, each graft limb can be introduced and advanced upstream until the cranial limb end is positioned near the associated aperture in the covering. The covering has a small size and is fixed to the expanded tubular body so that the apertures have a well-defined position and are open which makes it uncomplicated to insert the end of the catheter holding the limb through the aperture, whereafter the catheter is withdrawn in relation to the limb which expands and locks itself to the rim area of the aperture. When both limbs have been mounted the graft prosthesis occludes the aorta upstream of the aneurysm so that blood is only allowed to flow via the limbs into the first and second iliac arteries.

The limbs may preferably be kept in position on the prosthetic device simply by the radial outward pressure exerted by the limb on the rim of the associated aperture. In order to obtain high safety against loosening of a limb from the aperture it is, however, also possible that each graft limb at its cranial end is provided with a mounting means for gripping the covering surrounding the aperture, such as radially extending fingers or a collar surrounding and extending radially outwards from the cranial end opening of the limb when the latter is in its expanded shape mounted on the prosthetic device.

Mounting of the graft prosthesis can be further simplified by using an endovascular prosthetic device which prior to deployment in the vascular system is positioned contracted into the first state in an introducer catheter together with two preloaded guide wires each extending through one of the apertures in the covering. When the device has been positioned in the aorta and the introducer catheter has been removed, the two guide wires will extend into the first iliac artery. Then a wire with a gripping means is advanced upstream through the second iliac artery and engaged with one of the guide wires which is pulled out of the first and into the second iliac artery so that its caudal end extends out through the femoral puncture site. The graft limbs loaded in corresponding catheters are then inserted over the guide wires and advanced into the vascular system until the cranial limb end has passed the associated aperture, whereafter the catheter is withdrawn to allow the limb to expand. To complete the mounting of each limb, the limb is simply pulled backwards until the radially extending mounting means is in contact with the cranially positioned covering. This procedure is very simple and uncomplicated and can be carried out in a short time.

DETAILED DESCRIPTION

Figure 1:
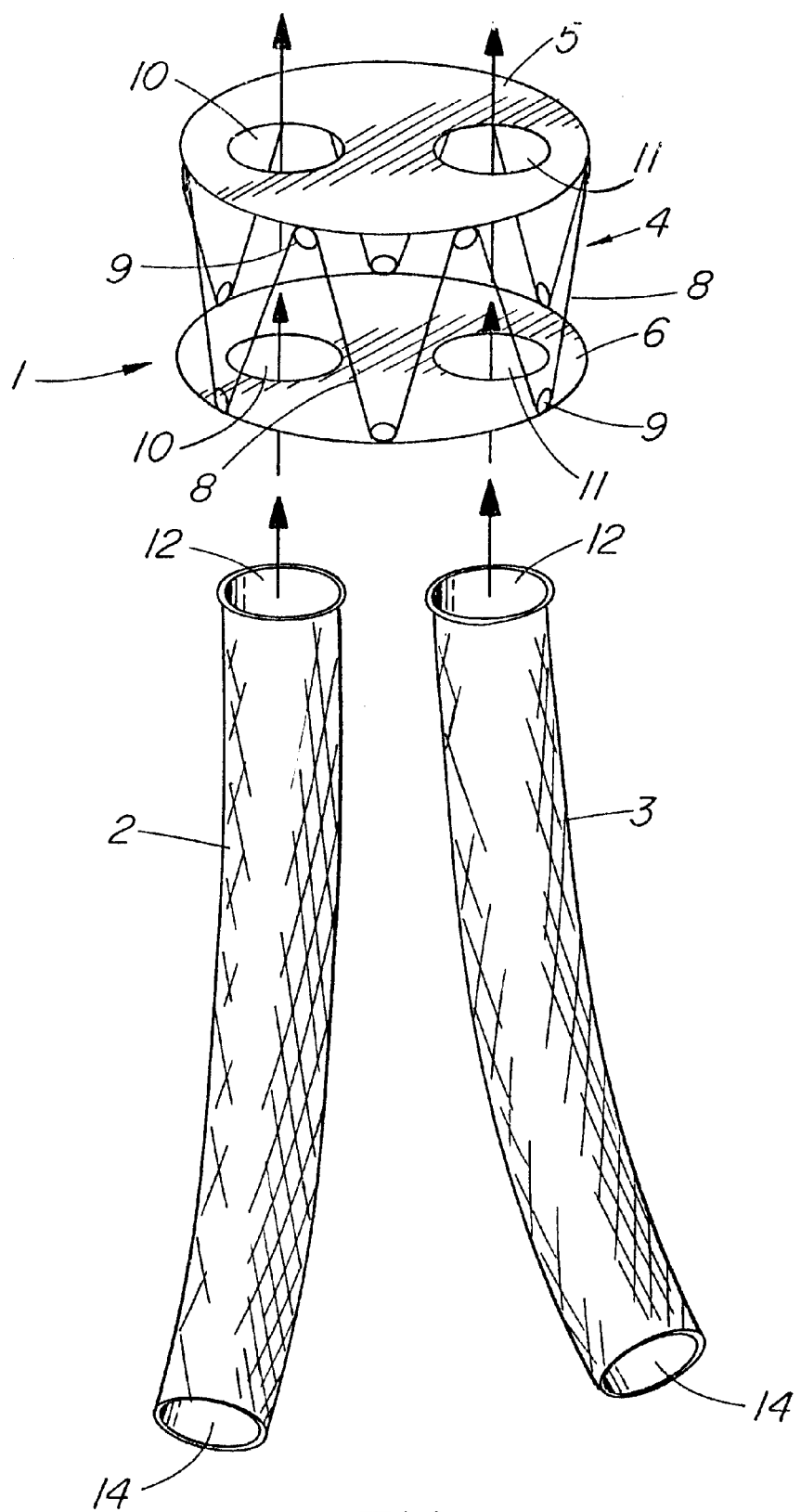
FIG. 1 shows a schematic view of a preferred embodiment of the three major components making up a graft prosthesis according to the invention.

In FIG. 1 is depicted an endovascular prosthetic device 1 and a first and a second graft limb 2, 3. Device 1 comprises a tubular frame or stent 4 and two coverings 5, 6 made of blood impermeable material. Examples of such materials are polyester (such as Dacron™), PTFE, polyurethane, polyethylene, propylene, nylon or another bio-compatible material capable of blocking for a blood flow. PTFE (polytetrafluoroethylene) is a preferred material because it is strong and completely biologically inert.

Stent 4 is made of filaments of stainless steel, nitinol, titanium, tantalum, a copper alloy (possibly coated with PTFE or polyester) or another biologically compatible material capable of maintaining an expanded shape inside the vessel in which the device is deployed, such as modified butadiene or another synthetic material with good resilient properties. In case the stent is self-expanding, nitinol is a preferred material due to its excellent elastic properties and ability to tolerate large elastic deformations. Stainless steel is also a preferable material, in particular if the stent is to be balloon dilated to its expanded shape. The stent may typically have an outer diameter in the expanded shape in the range from 15 to 30 mm, and the diameter is chosen in dependency of the internal diameter of the intact infrarenal aorta portion positioned upstream of the aneurysm. Smaller diameters, such as from 6 to 15 mm, can be chosen if the device is to be deployed in bifurcated vessels other that the abdominal aorta.

The filament or wire may typically have a diameter in the range of 0.016 to 0.05 inch (0.4 to 1.3 mm) when the tubular stent or frame body is made of a single length filament formed into a closed zig-zag configuration having an endless series of straight sections 8 joined by bends 9 at opposite ends of sections 8. In case the stent is made of plural helically wound and possibly interwoven, mutually crossing filaments, the diameter of the filaments may be smaller than mentioned, such as from 0.002 to 0.03 inch (0.05 to 0.76 mm).

At the bends 9 the filament may be simple arched, recurved arched or apertured with a small eyelet at each bend. The coverings 5, 6 may have a circular outer periphery fixed to the filament by suturing at the bends. If the filament bends are apertured, the periphery of the covering can be locked to the stent end by running a thread, filament or suture through the eyelets and stitching it through the covering in between the eyelets. An alternative fixation of the covering may be welding. The covering may also be multi-layered, and the layers may be fixed to one another after the filament bends have been inserted in between the layers. Each covering 5, 6 is provided with a first and a second aperture 10, 11, and the two first apertures 10 and the two second apertures 11 in coverings 5, 6 are aligned one above the other when the tubular body is in its expanded shape in order to allow insertion of the first and second graft limbs 2, 3 through the first apertures and the second apertures, respectively.

Each graft limb 2, 3 comprises one or more self-expandable stents of filament material similar to stent 4 and covered with a blood impermeable material which may be selected among the same type of materials as the coverings. The material may be a woven multifilament material or a coherent tube-like material. The graft limbs are contractible into a first shape having a smaller diameter for loading into an introducer sheath or catheter which preferably has an internal diameter of 14 French (4.67 mm) or less and an external diameter of 16 French (5.33 mm) or less, as this allows introduction by true percutaneous techniques. When the graft limb is released from the catheter by withdrawal of the catheter while being in position by a pusher means, it self-expands into a second shape as illustrated in FIG. 1.

Figure 9:
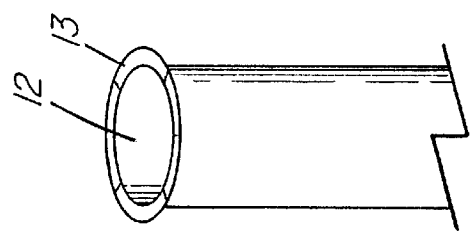
FIG. 9 is a perspective view of the cranial end of a graft limb shown in the expanded shape.
Figure 10:
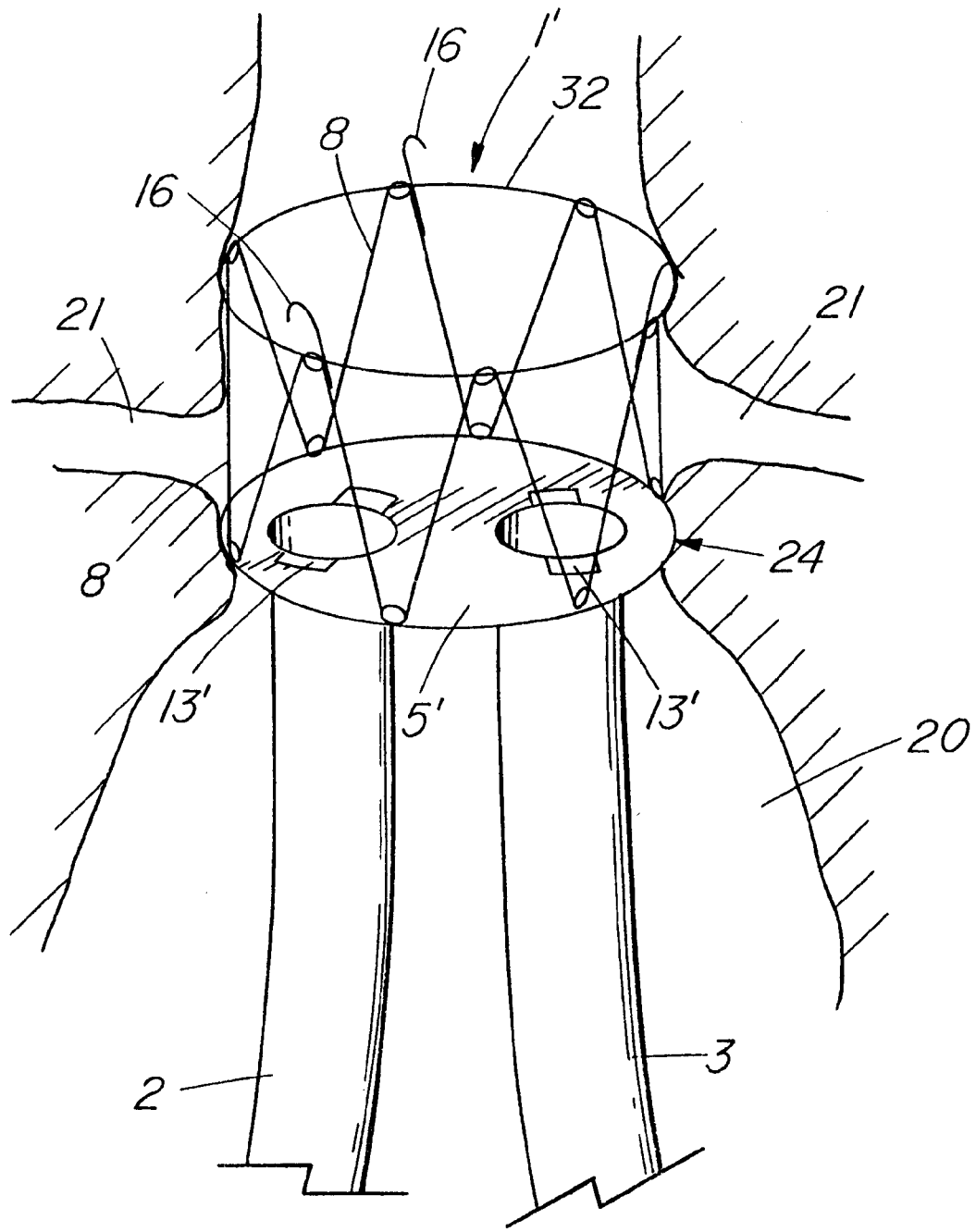
FIG. 10 is a cranial portion of a second embodiment of the prosthesis.

The graft limb has in the second expanded shape a cranial inlet opening 12 with slightly larger diameter than the diameter of the associated aperture in the cranial covering 5 in order to assure a hemostatic seal between the outer side of the graft and covering 5. It is possible to design the graft limb with a bell-shaped or flared cranial end which can be pulled backwards into sealing abutment with the rim of the aperture. In this case the cranially protruding larger diameter portion of the graft limb acts as a mounting means. Alternatively, the mounting means may be designed as a collar 13 protruding radially outwards from the cranial end of the limb, as shown in FIG. 9. This brings the advantage that inlet opening 12 is substantially flush with covering 5 in the finished graft prosthesis. The mounting means may also be a number of radially projecting spikes or laps 13', as seen in FIG. 10.

At its caudal end the graft limb has an outlet opening 14 to be mounted in the common iliac artery or in another vessel downstream of the bifurcation in the relevant bifurcated vessel.

The drum-shaped prosthetic device 1 can be manufactured and delivered in several sizes, such as with external diameters of 15, 20, 25 and 30 mm, and in several lengths, such as 15, 20, 25 and 30 mm, and the graft limbs may be delivered in several sizes, such as with caudal end diameters of 8, 10, 12, 14 and 16 mm, and possibly also in different lengths, if it should be undesirable to cut a long limb to the desired length prior to the insertion. When an abdominal aorta aneurysm repair is to be performed, the correctly sized parts may be picked from stock in order to easily obtain a graft prosthesis specifically sized to the patient. By choosing a correct diameter of the graft limb, the caudal end of the limb will in most cases fit hemostatic sealingly into the common iliac artery. Should an additional safety against caudal leaks into the aneurysm be desired then it is also possible to place a relatively strong stent inside the caudal end of the limb.

Figure 2:
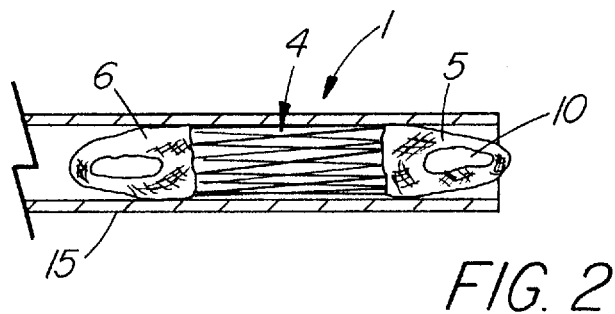
FIG. 2 shows a part-sectional side view of a prosthetic device loaded in a introducer catheter.

The prosthetic device 1 is loaded into a first introducer sheath or catheter 15 (FIG. 2) prior to insertion into the vascular system. The two coverings 5, 6 can be extended away from the tubular frame body when loading in order to minimize the outer diameter of the device in its contracted first shape. This allows the device to be loaded in a catheter having an inner lumen of 14 French or less, and so all three parts of the graft prosthesis can be introduced by true percutaneous techniques. The advantage is that the whole procedure of making the aneurysm repair can be performed without general anesthesia or major surgery and with a minimum of trauma to the patient.

The tubular frame body can be provided with several surgical barbs 16 (see in FIG. 10) for anchoring the device into the vascular wall. Barbs 16 can be fixed to the straight filament sections by welding, soldering or the like, well known prior art techniques. Additionally, the barbs can also be mechanically affixed to the straight filament sections by wrapping the intermediate portion of the barb one or more times around a straight filament section.

The method for repairing the abdominal aorta aneurysm with the inventive graft prosthesis is hereinafter described in detail.

Figure 3:
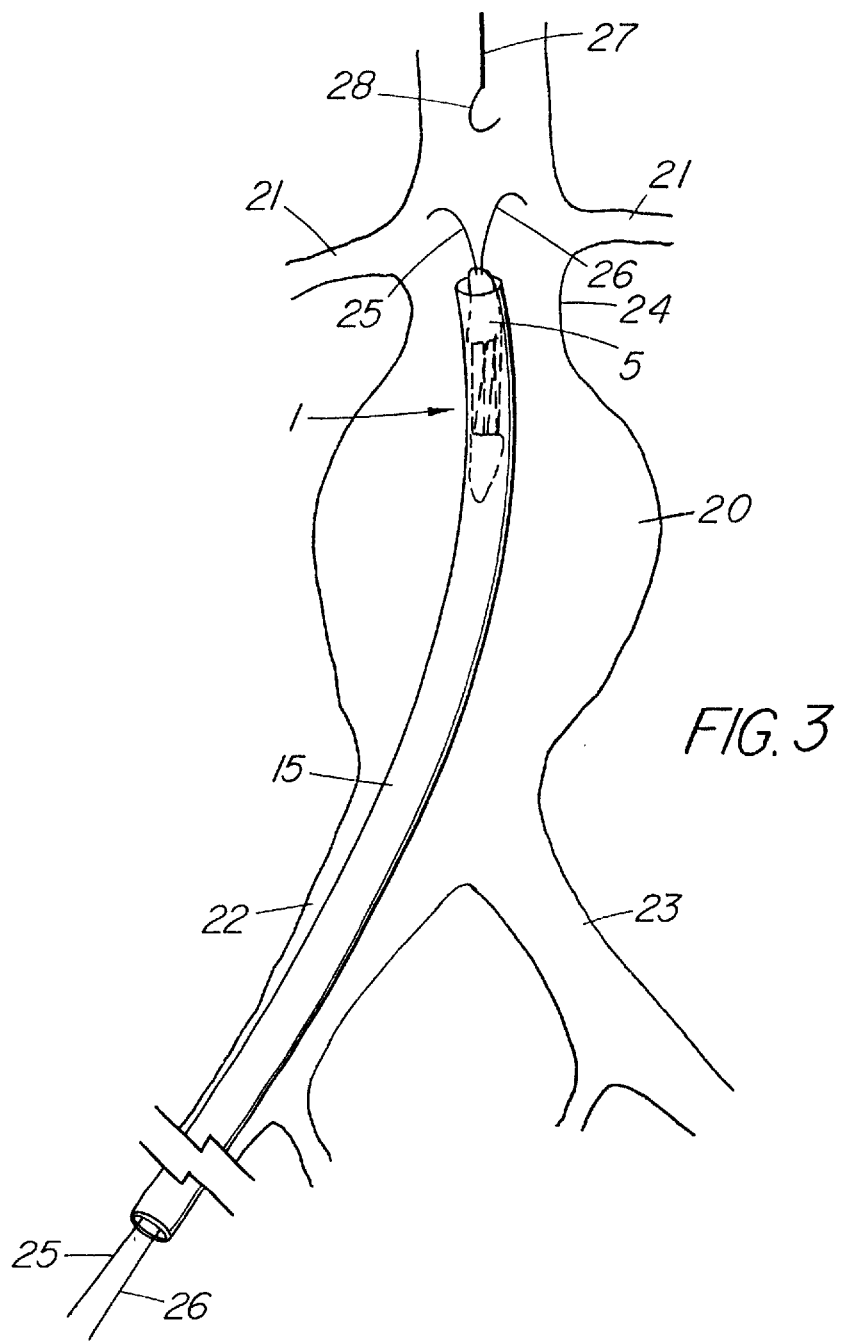
FIG. 3–7 illustrate successive steps of deploying the prosthesis for repairing an abdominal aorta aneurysm.

As depicted in FIG. 3, an aneurysm 20 is illustrated in the infrarenal portion of the aorta abdominal is positioned between the renal artery branches 21 and the bifurcation into the first and second common iliac arteries 22, 23. By use of the Seldinger technique the introducer catheter 15 with a preloaded prosthetic device 1 is transfemorally introduced and advanced via the first common iliac artery 22 to the undamaged infrarenal aortic portion 24 upstream of the aneurysm. It is preferred, but not required, that a first and a second guide wire 25, 26 is preloaded together with device 1 in such a manner that first guide wire 25 extends through the first apertures 10 in coverings 5, 6, and second guide wire 26 extends through the second apertures in coverings 5, 6.

When the tip of catheter 15 is in position at aortic portion 24, the prosthetic device 1 is released from the catheter. This may be done by advancing a pusher up through the catheter to push out the device, or by axillarily introducing a catheter with a wire 27 having a gripping means 28 in the downstream direction until it is positioned near the tip of catheter 15, whereafter the gripping means is manipulated into engagement with device 1, preferably by passing gripping means 28 through the first and second apertures in the cranial covering 5, and wire 27 is pulled in the cranial direction so that device 1 leaves the introducer catheter, or by a combination of these two techniques.

Figure 4:
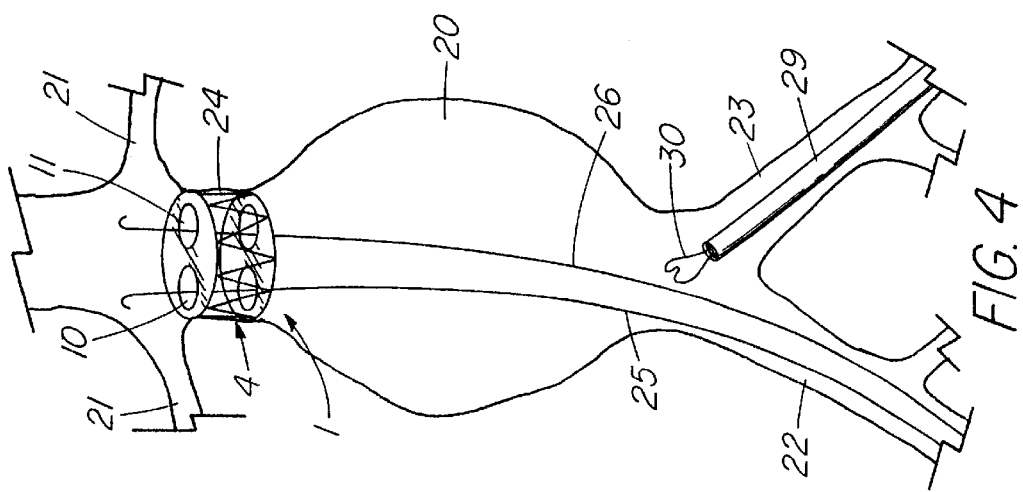

When the prosthetic device is brought out of the first catheter, the tubular frame expands by self-expansion towards a second shape with larger diameter simultaneously with unfolding of the two coverings 5, 6. During the expansion, the frame and the outer rims of the two coverings are brought into contact with the aorta and exert a radial outward pressure on aortic portion 24, as depicted in FIG. 4. In its second shape frame 4 has a larger external diameter than the internal diameter of aortic portion 24 and the frame will consequently widen portion 24 and thus create a hemostatic seal between the outer rims of coverings 5, 6 and aortic portion 24. The first catheter is then retracted leaving the first and second guide wires and device 1 in place, where the device partly occludes the aorta, as the blood flow only occurs through the apertures in coverings 5, 6.

By use of the Seldinger technique a catheter 29 with a wire having a gripping means 30 is transfemorally introduced and advanced through the second common iliac artery 23. The gripping means is engaged with the second guide wire 26 and the caudal end thereof is pulled out of first iliac artery 22 and into the second iliac artery and further out through the femoral puncture site.

Figure 6:
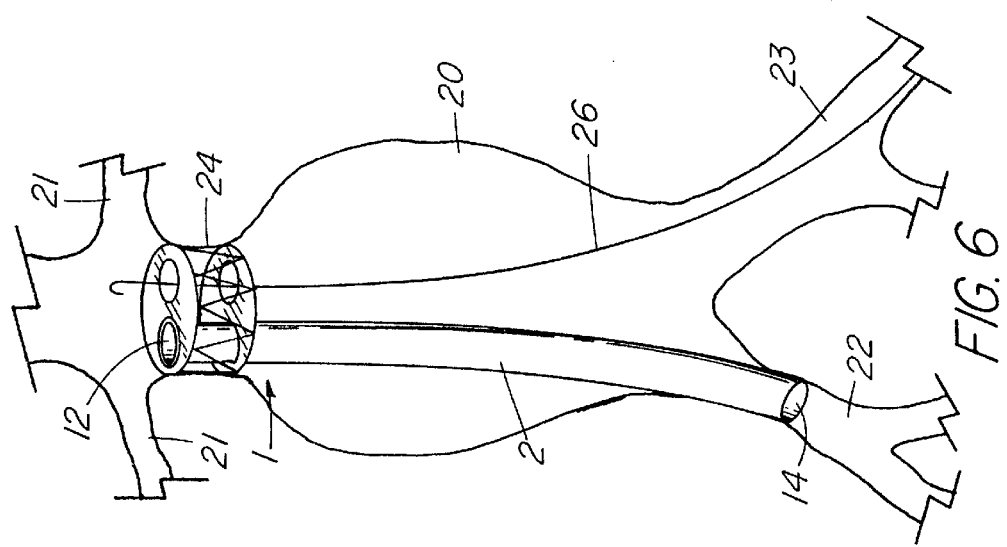
Figure 5:
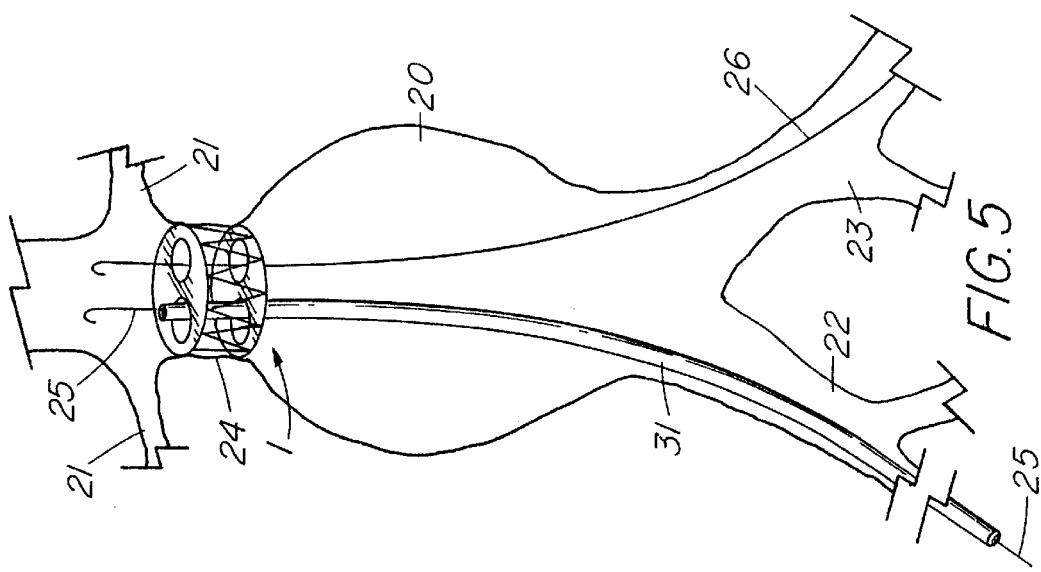
Figure 8:
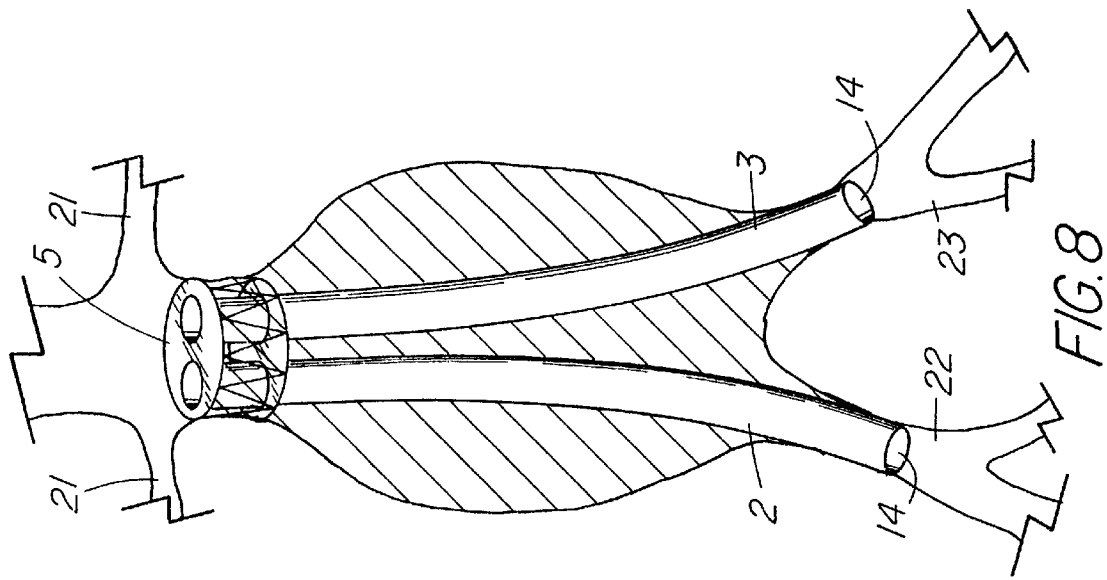
FIG. 8 shows a side view of the installed prosthesis several days after deployment.
Figure 7:
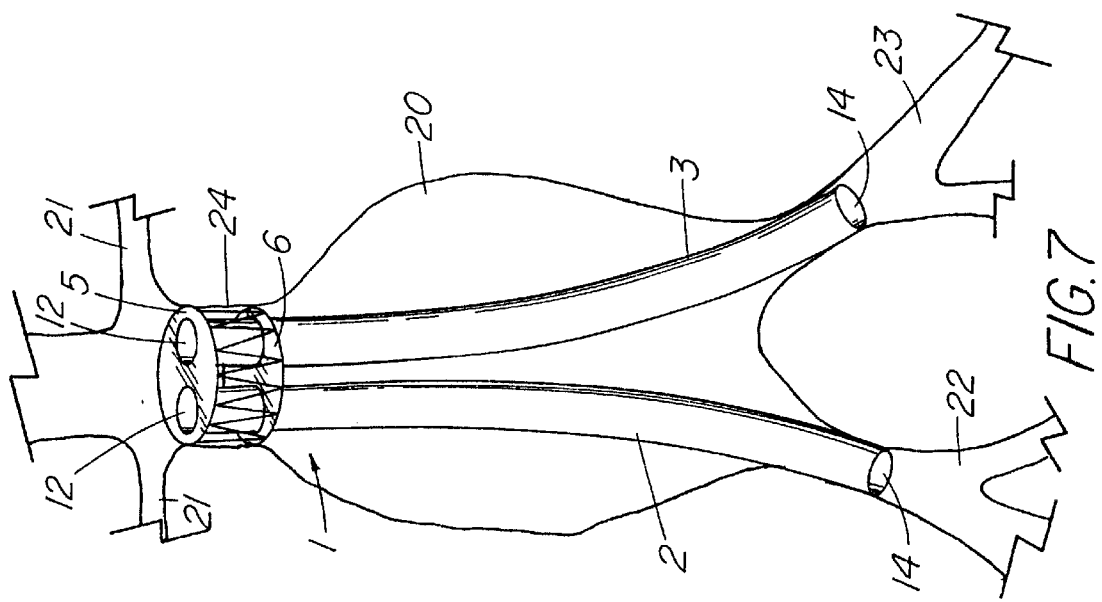

Then a second introducer catheter 31 with the preloaded first graft limb 2 is advanced over first guide wire 25 up through the two first apertures in device 1, as depicted in FIG. 5, and the first guide wire is retracted. A pusher is advanced through second catheter 31 and when the cranial end of first limb 2 begins to expand outside the catheter tip, catheter 31 is retracted in a controlled manner. Simultaneously, the push on the pusher is maintained so that the first graft limb expands to the correct positions in device 1 and in the first common iliac artery, as depicted in FIG. 6. Then the procedure is repeated with a third catheter with the preloaded second graft limb 3 which are advanced over the second guide wire up through the two second apertures in device 1. When the second limb 3 has been expanded into position, the procedure of deploying the graft prosthesis is complete, as depicted in FIG. 7, and the blood flow to the aneurysm is completely blocked. During the following hours and days a hemostatic reaction takes place in the cavity surrounding the graft prosthesis resulting in a complete blocking of the cavity as depicted in FIG. 8. During this period, the device 1 fulfils an important function to completely occlude the cavity from the upstream aortic portion, and also when the patient moves.

When aortic portion 24 is very short it may be an advantage to use a slightly varied embodiment of device 1 in the graft prosthesis. The prosthetic device 1' shown in FIG. 10 has only one covering 5' mounted to the caudal end of the frame body. Due to the very open side wall of the tubular frame the blood flow to the renal artery branches may be upheld unhindered despite placement of device 1' outside these branches. At the cranial end of the tubular body a filament, suture or thread 32 is mounted to the bends in order to restrict the maximum expanded diameter of this frame end to approximately the same diameter as the caudal end. Apart from the slightly higher placement of device 1' in the aorta and the mounting of the graft limbs to the covering at the caudal end of the frame body, mounting of the graft prosthesis occurs as described above.

The above mentioned details in the various embodiments can be combined at choice into further embodiments, and other variations are possible within the scope of the claims, such as using in the graft limbs and/or in device 1 stents having filaments knot into various cell shapes or stents produced from apertured sheets of material.

What is claim is:

1. An endovascular prosthetic device, comprising:
    at least one expandable tubular frame body, said frame body being contractible into a first shape with a smaller diameter for introduction to a vascular site and being radially expandable into a second shape having a larger diameter and an inner lumen extending from one end to the other end of the tubular frame; and
    at least one covering of bio-compatible material provided for said frame body, wherein said covering extend freely across said inner lumen of the tubular frame body from a covering periphery secured to said tubular frame and has a first and a second aperture each sized to hold graft limbs, and each of said apertures has a diameter of less than half said larger diameter of the frame body, and wherein said covering is adapted to be spread out by the expansion of said tubular frame to extend orthogonally across said inner lumen, said covering having a circular-shaped outermost periphery.

2. The endovascular prosthetic device according to claim 1, wherein said at least one covering is positioned at one end of said tubular body when said tubular body is in said expanded second shape.

3. The endovascular prosthetic device according to claim 1, wherein said at least one covering is positioned at a first and a second end of said tubular body.

4. The endovascular prosthetic device according to claim 1, wherein said tubular body comprises a flexible filament formed into a closed zig-zag configuration having an endless series of straight sections joined by bends at opposite ends of said straight sections.

5. The endovascular prosthetic device according to claim 4, wherein said at least one covering is fixed to one end of said body at said bends, and wherein said tubular body is without covering on a periphery thereof extending between the body ends.

6. An endovascular graft prosthesis for arrangement at an aneurysm positioned in the vicinity of a bifurcation in a vascular system, said vascular system having a main lumen and a first and a second branch lumen, said graft prosthesis comprising the endovascular prosthetic device according to claim 1 with the tubular frame body for arrangement in said main lumen and a first and a second graft limb, said frame body being contractible into said first shape with said smaller diameter for introduction to the vascular site upstream of the aneurysm,
    wherein said first limb has a cranial end for mounting at one of said apertures and a caudal end for arrangement in said first branch lumen, and said second limb has a cranial end for mounting at an other of said apertures and a caudal end for arrangement in said second branch lumen, and wherein said covering is a hindrance to blood flowing past said frame body except for blood flowing into said first and second graft limbs mounted at the first and the second apertures.

7. The endovascular graft prosthesis according to claim 6, wherein said covering is positioned at one end of said frame body when said frame body is in said expanded second shape.

8. The endovascular graft prosthesis according to claim 6, wherein said at least one covering is positioned at a first and a second end of said frame body.

9. The endovascular graft prosthesis according to claim 6, wherein said frame body comprises a flexible filament formed into a closed zig-zag configuration having an endless series of straight sections joined by bends at opposite ends of said straight sections.

10. The endovascular graft prosthesis according to claim 9, wherein said covering is fixed to one end of said body at said bends, and wherein said frame body is without covering on a periphery thereof extending between the body ends.

11. The endovascular graft prosthesis according to claim 6, wherein each of said first and second graft limbs at said cranial end has a mounting means for gripping the covering surrounding said aperture.

12. The endovascular graft prosthesis according to claim 11, wherein each of said first and second graft limbs is contractible into a first shape with a smaller diameter for introduction to the vascular site where said prosthetic device is placed and is expandable into a second shape with a larger diameter.

13. The endovascular graft prosthesis according to claim 12, wherein said mounting means extends radially from the cranial end of the graft limb to a diameter larger than said diameter of the aperture.

14. The endovascular graft prosthesis according to claim 13, wherein said mounting means is a collar surrounding a cranial end opening of said graft limb.

15. The endovascular graft prosthesis according to claim 12, wherein each of said first and second graft limbs prior to deployment in the vascular system is positioned contracted into said first state in an introducer catheter having an outer diameter of 16 French or less.

16. The endovascular graft prosthesis according to claim 6, wherein said endovascular prosthetic device prior to deployment in the vascular system is positioned contracted into said first state in an introducer catheter having an outer diameter of 16 French or less.

17. The endovascular graft prosthesis according to claim 6, wherein said endovascular prosthetic device prior to deployment in the vascular system is positioned contracted into said first state in an introducer catheter together with two preloaded guide wires each extending through one of said apertures in said covering.

18. The endovascular graft prosthesis according to claim 6, wherein said frame body is self-expanding from said first to said second state.

19. The endovascular graft prosthesis according to claim 6, wherein said frame body is provided with anchoring means.

20. A method for repairing an abdominal aortic aneurysm in an aorta having a lumen and bifurcating into a first and a second iliac artery, comprising the steps of:

providing a first catheter with a preloaded endovascular prosthetic device comprising at least one expandable tubular frame body, said frame body being contractable into a first shape with a smaller diameter for introduction to a vascular site and being radially expandable into a second shape having a larger diameter and an inner lumen and at least one covering of bio-compatible material provided for said frame body, wherein said covering extends across said inner lumen of the tubular frame body and has a first and a second aperture, each of said apertures has a diameter of less than half said larger diameter of the frame body, and wherein said covering is adapted to be spread out by the expansion of said tubular frame, and said first catheter also with a first and a second preloaded guide wire inserted through said first and second aperture, respectively, introducing said first catheter into said first iliac artery and advancing it to a position upstream of the aneurysm, releasing said endovascular prosthetic device from said first catheter and expanding the device so that at least part of the periphery of the frame body is in contact with the aorta upstream of said aneurysm and so that said covering extends across said aorta lumen at said frame body, introducing a wire with a gripping means into said second iliac artery, gripping said second guide wire and pulling a caudal end section of said second guide wire from said first iliac artery into said second iliac artery , advancing a second catheter with a preloaded first graft limb over said first guide wire until a cranial end of said limb has passed said first aperture, releasing said first graft limb from said second catheter so that said cranial limb end is mounted at said first aperture and a caudal end of said first graft limb is positioned in said first iliac artery, advancing a third catheter with a preloaded second graft limb over said second guide wire until a cranial end of said limb has passed said second aperture, and releasing said second graft limb from said third catheter so that said cranial limb end is mounted at said second aperture and a caudal end of said second graft limb is positioned in said second iliac artery.

21. The method according to claim 20, wherein said endovascular prosthetic device is released from said first catheter by use of a pusher advanced through said first catheter.

22. The method according to claim 20, wherein said endovascular prosthetic device is released from said first catheter by use of a wire having a gripping means, said wire being axially introduced and advanced to said first catheter where the gripping means is engaged with said prosthetic device and used to pull s aid prosthetic device out of said first catheter.

23. The method according to claim 20, wherein said endovascular prosthetic device has one covering attached to each end of said frame body and is preloaded in said first catheter so that each covering extends away from said frame body.

24. The endovascular graft prosthesis according to claim 1, wherein said tubular frame body defines single large apertures at opposite ends of said inner lumen, when expanded.

25. The endovascular graft prosthesis according to claim 1, wherein each said at least one said covering is secured to said tubular frame at a peripheral edge of said covering and extends freely therefrom.

* * * * *